United States Patent [19]

Misra

[11] Patent Number: 5,135,939
[45] Date of Patent: Aug. 4, 1992

[54] HETEROCYCLIC KETONE PROSTAGLANDIN ANALOGS

[75] Inventor: Raj N. Misra, Hopewell, N.J.

[73] Assignee: E. R. Squibb & Sons, Inc., Princeton, N.J.

[21] Appl. No.: 646,975

[22] Filed: Jan. 28, 1991

[51] Int. Cl.$^5$ .................. A61K 31/42; A61K 31/415; C07D 413/08; C07D 403/08
[52] U.S. Cl. ................... 514/374; 514/397; 548/215; 548/336
[58] Field of Search ............... 548/215, 336; 514/374, 514/397

[56] References Cited

U.S. PATENT DOCUMENTS

| | | | |
|---|---|---|---|
| 4,416,896 | 11/1983 | Nakane et al. | 424/285 |
| 4,418,076 | 11/1983 | Nakane et al. | 424/285 |
| 4,463,015 | 7/1984 | Haslanger et al. | 424/285 |
| 4,474,804 | 10/1984 | Das et al. | 424/285 |
| 4,522,949 | 6/1985 | Das et al. | 514/469 |
| 4,536,513 | 8/1985 | Das et al. | 514/469 |
| 4,663,336 | 5/1987 | Nakane et al. | 514/381 |
| 4,663,337 | 5/1987 | Das et al. | 514/382 |

OTHER PUBLICATIONS

As Belo Bioorg Chem, Apr. 3, 1981-SU278256 (Nov. 23, 1987) (1988).
Chem Abs. SA Selects: Prostaglandins Issue 12, 1988 108:198903m. Kuz'mitskii, B. B. et al.
CA Selects: Prostaglandins, Issue 12, 1988, 108:204363d, Lakhvich, F. A. et al.

Primary Examiner—Mary C. Lee
Assistant Examiner—Joseph K. McKane
Attorney, Agent, or Firm—Timothy J. Gaul

[57] ABSTRACT

Prostaglandin analogs useful in treating thrombotic and vasospastic disease having the structural formula

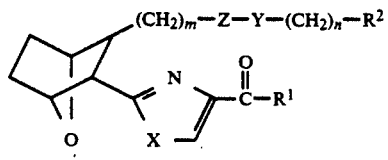

wherein:
m is 1, 2, or 3;
n is 0, 1, 2 or 3;
$R^1$ is hydrogen, alkyl, alkenyl, alkynyl, aralkyl, aryl cycloalkyl, cycloalkylalkyl, cycloheteroalkyl, cycloheteroalkylalkyl, heteroaryl or heteroarylalkyl, each of $R^1$ being unsubstituted or optionally substituted with alkyl, aryl, cycloalkyl, or cycloalkylalkyl;
$R^2$ is $CO_2R$ $CONHSO_2R^3$, $CONHR^4$;
R is hydrogen, alkyl, or alkali metal;
X is O or NH;
Y is —O—, a single bond or vinylene, except that Y cannot be —O— when n is O;
Z is —CH=CH—, —(CH$_2$)$_2$—, or

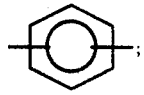

and the remaining symbols are as defined in the specification.

12 Claims, No Drawings

HETEROCYCLIC KETONE PROSTAGLANDIN ANALOGS

FIELD OF THE INVENTION

This invention relates to prostaglandin analogs useful as thromboxane $A_2$ receptor antagonists.

BRIEF DESCRIPTION OF THE INVENTION

A compound of the formula

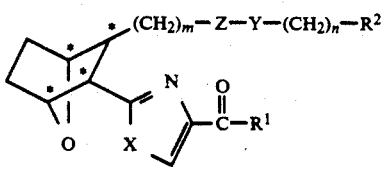
I is a thromboxane $A_2$ ($TXA_2$) receptor antagonist or a combined thromboxane $A_2$ receptor antagonist/thromboxane synthetase inhibitor. Compound I is useful, for example, in treating thrombotic or vasospastic disease. In compound I and throughout this specification, the symbols above are defined as follows:

m is 1, 2, or 3;
n is 0, 1, 2 or 3;
X is O or NH;
Y is —O—, a single bond or vinylene, except that Y cannot be —O— when n is 0;
Z is —CH=CH—, —($CH_2$)$_2$—, or

$R^1$ is hydrogen, alkyl, alkenyl, alkynyl, alkaryl, aralkyl, aryl, cycloalkyl, cycloalkylalkyl, cycloheteroalkyl, cycloheteroalkylalkyl, heteroaryl or heteroarylalkyl, each of $R^1$ being unsubstituted or optionally substituted with alkyl, aryl, cycloalkyl, or cycloalkylalkyl;
$R^2$ is $CO_2R$, $CPNHSO_2R^3$, or $CONHR^4$;
R is hydrogen, alkyl, or alkali metal;
$R^3$ is alkyl, aryl or aralkyl; and
$R^4$ is hydrogen, alkyl, aryl, aryl or aralkyl.

Thus, the compounds of the invention include the following types of compounds, which are preferred:

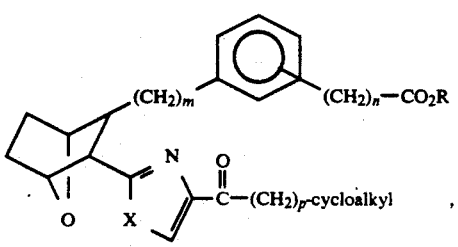
I(A)

and

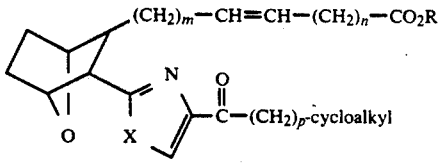
I(B)

wherein X, R, and n are as defined above and p is an integer from 1 to 7. Most preferred are those compounds wherein R' is hydrogen, m is 1, n is 2, p is 5, and the cycloalkyl group is cyclohexyl.

DETAILED DESCRIPTION OF THE INVENTION

DEFINITION OF TERMS

The term "alkyl" or "alk" includes both straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" or "Ar" refers to monocyclic or bicyclic aromatic groups containing from 6 to 10 carbons in the ring portion, such as phenyl and naphthyl, which may include 1 or 2 substituents on either the phenyl or naphthyl such as alkyl, trifluoromethyl, halogen (Cl, Br, I or F), alkoxy, arylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The terms "alkoxy" and "aralkoxy" refer to the above alkyl and aralkyl groups linked to an oxygen atom.

The term "halogen" or "halo" refers to chlorine, bromine, fluorine or iodine, with chlorine being preferred.

The term "alkenyl" as employed herein with respect to the $R^1$ substituent includes a carbon chain of up to 12 carbons, preferably 3 to 10 carbons, having at least one double bond, which will be separated from "N" by at least one saturated carbon moiety such as —($CH_2$)$_q$— where q can be 1 to 14, such as 2-propenyl, 2-butenyl, 3-butenyl, 2-pentenyl, 4-pentenyl and the like, and may include a halogen substituent such as I, Cl, or F.

The term "alkynyl" as employed herein with respect to the $R^1$ substituent includes a carbon chain of up to 16 carbons, preferably 3 to 10 carbons, having at least one triple bond, which will be separated from "N" by at least one saturated carbon moiety such as —($CH_2$)$_q$— wherein q can be 1 to 14, such as 2-propenyl, 2-butenyl, 3-butenyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked through a carbon atom either beta or gamma to a heteroatom, such as

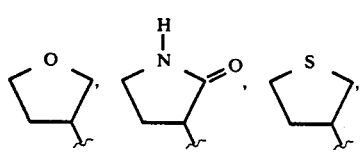

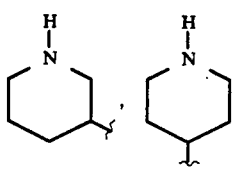

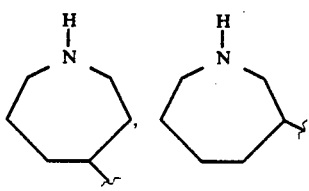

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a heteroatom, such as

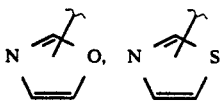

and the like.

The term "cycloheteroalkylalkyl" as used herein with respect to $R^1$ refers to 5-, 6- or 7-membered saturated rings that include 1 or 2 heteroatoms such as nitrogen, oxygen or sulfur, and are linked through a $(CH_2)_x$ chain wherein x is 1 to 12, preferably 1 to 8, such as

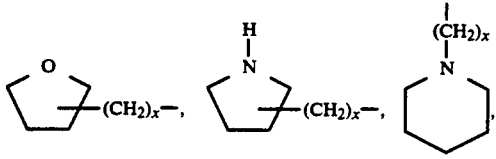

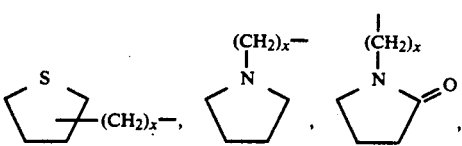

-continued

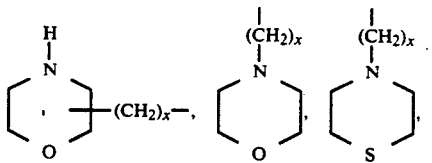

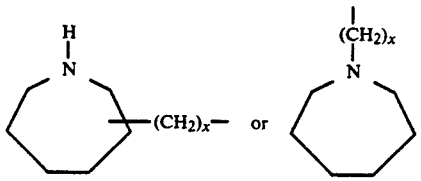

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and are linked through a $-(CH_2)_x-$ chain where x is 1 to 12, preferably 1 to 8, such as

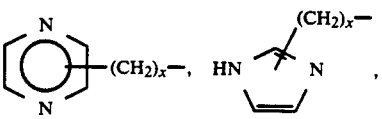

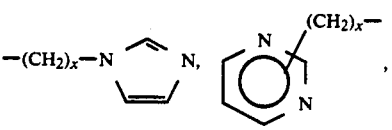

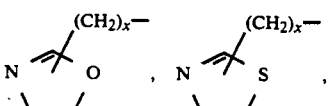

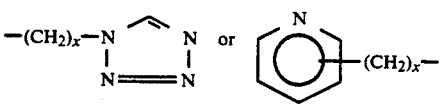

and the like.

Processes of Preparation

Compounds of the invention wherein Y is a single bond are prepared starting with bromophenylalkyl alcohol A

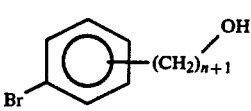

A wherein n is 1, 2, 3 or 4. Compound A is treated with a protecting compound (e.g., t-butylchlorodiphenylsilane) in the presence of an amine base (e.g., triethylamine) and an inert solvent, employing conventional procedures, to form the protected bromophenylalkyl compound B

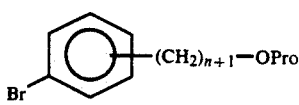

wherein Pro represents a protecting group. Examples of protecting compounds suitable for use herein in reacting with bromophenalkyl alcohol A include but are not limited to

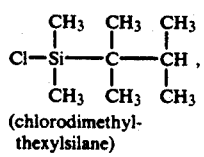

(chlorodimethyl-thexylsilane)

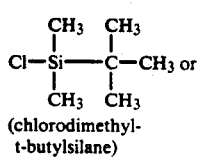

(chlorodimethyl-t-butylsilane)

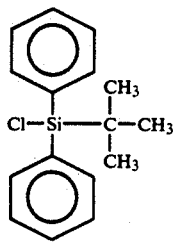

(t-butylchlorodiphenylsilane)

and the like.

The protected compound B then undergoes a metal-halogen exchange reaction by treatment with, for example, t-C$_4$H$_9$Li or n-C$_4$H$_9$Li in the presence of diethyl ether or tetrahydrofuran (THF) at about $-100°$ to about $0°$ C., or is preferably subjected to a Grignard reaction by treatment with magnesium in the presence of an inert organic solvent (e.g., THF or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054 or in Patel et al., "(exo,exo)-7-oxabicyclo[2.2.1] heptane-2,3-dimethanol, monoacyl ester, diacyl ester and enzymatic hydrolysis thereof", U.S. Ser. No. 629,780, filed Dec. 18, 1990) of the structure C

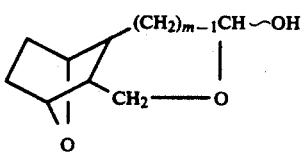

employing a molar ratio of C:B from about 1:2 to about 1:4, in the presence of an inert organic solvent such as THF at about $-78°$ to about $25°$ C. to form the condensed 7-oxabicycloheptane compound

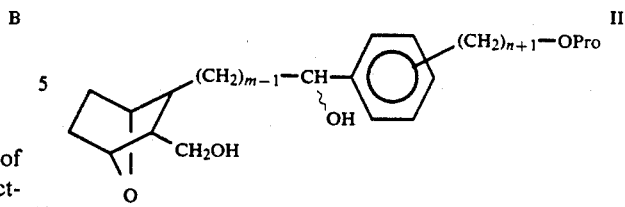

The condensed compound II is then subjected to hydrogenolysis by treatment with hydrogen in the presence of a catalyst (e.g., palladium hydroxide on charcoal) in acetic acid or an inert organic solvent (e.g., ethyl acetate) to form the alcohol

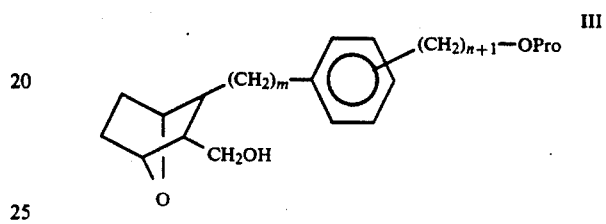

When the protecting group (Pro) in alcohol III is thexyldimethylsilyl or t-butyldimethylsilyl, alcohol III may be reacted with an acetylating agent (e.g., acetic anhydride) in the presence of pyridine and dimethylaminopyridine (DMAP) to form

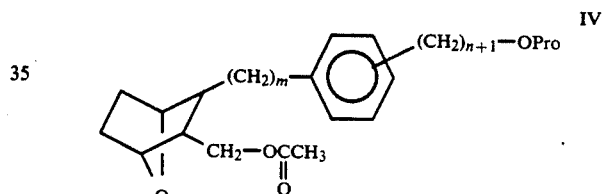

Acetylated compound IV is then reacted with Jones reagent (see Fieser and Fieser, *Reagents in Organic Synthesis*, Vol. 1, p. 242) at about $-10°$ to $10°$ C. in acetone to form an acetate-acid

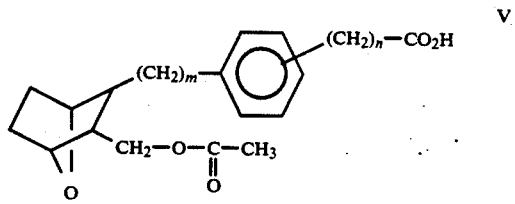

The acetate-acid V is reacted with an aqueous alkali metal hydroxide in tetrahydrofuran or excess methyllithium to form an alcohol-acid

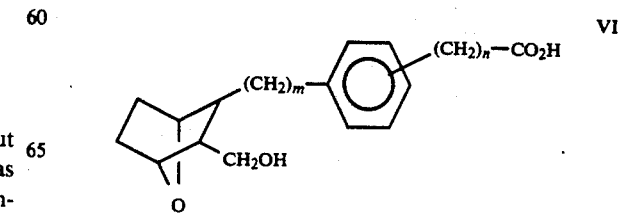

Alcohol-acid VI is then esterified with an acidic alcohol (e.g., HCl/CH₃OH) at about −10° to 10° C. to form an alcohol ester

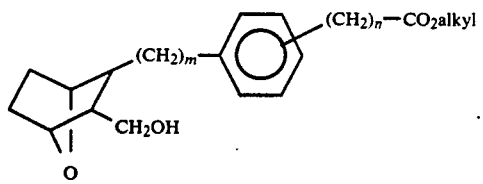

Alcohol-ester VII is oxidized with Jones reagent at about −10° to 10° C. in acetone to form an acid-ester

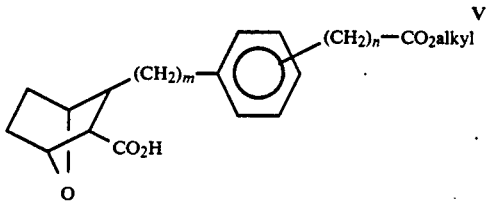

Acid VIII undergoes a carbodiimide coupling reaction in an inert organic solvent (e.g., tetrahydrofuran) with amine hydrochloride

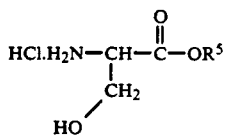
D wherein R⁵ is aralkyl, such as benzyl, in the presence of dicyclohexylcarbodiimide (DCC) or 1-(3-dimethylaminopropyl)-3-ethylcarbodiimide hydrochloride (WSC) and 1-hydroxybenzotriazole (HOBT) and triethylamine under an inert atmosphere such as argon employing a molar ratio of D:VIII of about 1.2:1 to about 1:1, to form hydroxyamide

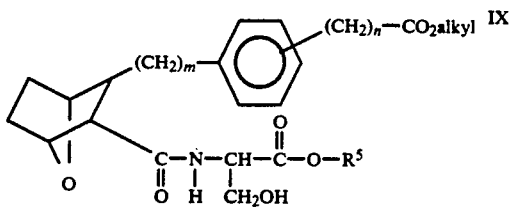

Hydroxyamide IX is then subjected to cyclodehydration in an inert organic solvent (e.g., tetrahydrofuran, acetonitrile or chloroform) under an inert atmosphere (e.g., argon) with triphenylphosphine (employing a molar ratio of V:triphenylphosphine of from about 0.8:1 to about 1:1) and carbon tetrachloride in the presence of an amine base (e.g., triethylamine or diisopropylethylamine) to form oxazoline

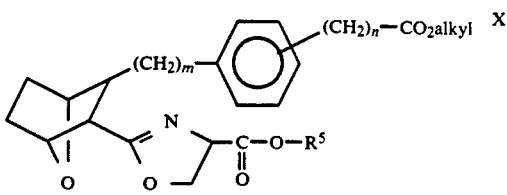

Oxazoline X is oxidized by treatment with manganese dioxide, preferably nickel peroxide or cupric bromide (which is preferred) and 1,8-diazabicyclo[5.4.0]undec-7-ene (DBU) to form oxazole

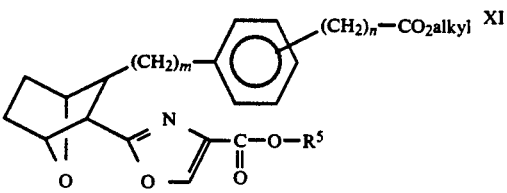

The cupric bromide oxidation is carried out at about 20° to 70° C. in a molar ratio 2:1 to 6:1 cupric bromide:oxazoline X and about 1:1 to 1:3 cupric bromide:DBU in an inert solvent (e.g., ethyl acetate) or solvent mixture (e.g., ethyl acetate/chloroform 1:1 v/v, which is preferred). See also Nakagawa, *J. Org. Chem.* 27 (1962), 1597.

Oxazole XI is converted to the corresponding acid by treatment with palladium hydroxide on charcoal in the presence of an inert solvent (e.g., ethyl acetate) to form the acid

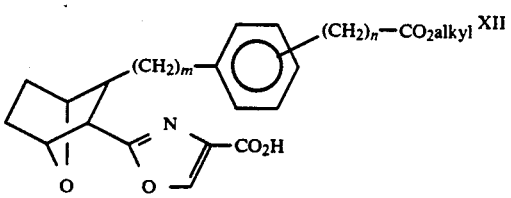

Acid XII is converted to the corresponding acid chloride by treatment, for example, with oxalyl chloride, optionally in the presence of catalytic amounts of dimethylformamide, and a solvent such as benzene, toluene, or methylene chloride to form the acid chloride

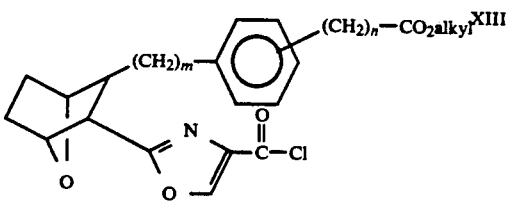

Acid chloride XIII is treated with a Grignard reagent
E

in the presence of zinc chloride and ether in an organic solvent (e.g., benzene) at about 20° to 30° C. to form compound I wherein R² is CO₂R and R is alkyl.

Alternatively, when X is NH, acid VIII undergoes a coupling reaction with an amine

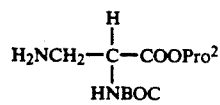

(wherein BOC is t-butyloxycarbonyl and Pro² is a protecting group such as benzyl) in the presence of a coupling agent such as WSC and HOBT in methylene chloride for about 12 to 90 hours, employing an acid:amine molar ratio of about 1.2:1 to about 1:1. The resulting amide undergoes a thionation reaction with Lawesson's reagent in the presence of benzene at about 50° to 75° C. for about 1 to 4 hours to form an ester

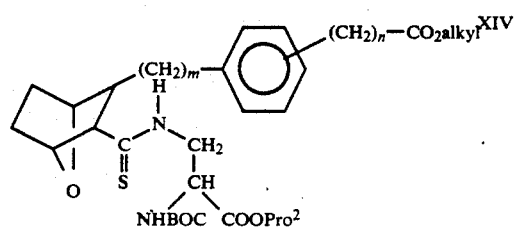

The ester XIV is cyclized in an inert solvent (e.g., acetonitrile, methylene chloride or THF) with triphenylphosphine in an ester XIX:triphenylphosphine molar ratio of about 0.8:1 to 1:1, along with carbon tetrachloride in the presence of an amine base (e.g., triethylamine or diisopropylethylamine) to form an imidazoline

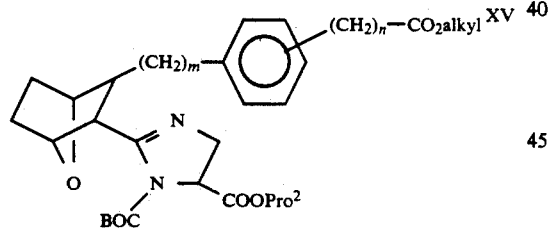

Imidazoline XV is then deprotected to remove the Pro² protecting group, using conventional procedures to form an acid

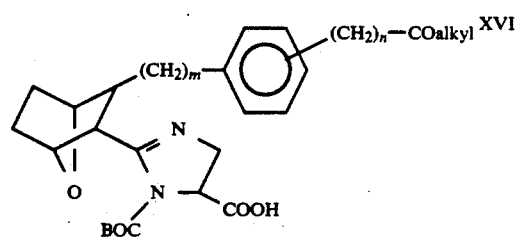

Next, the acid XVI is converted to the acid halide and treated with Grignard reagent as described for compounds XII and XIII to form

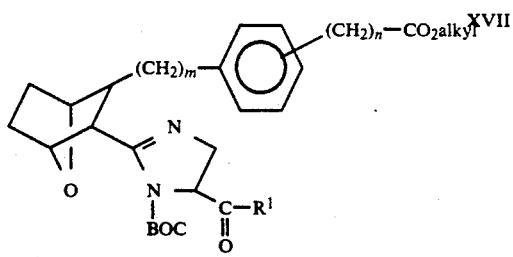

Compound XVII in methylene chloride is then treated with trifluoroacetic acid to remove the BOC group and forms

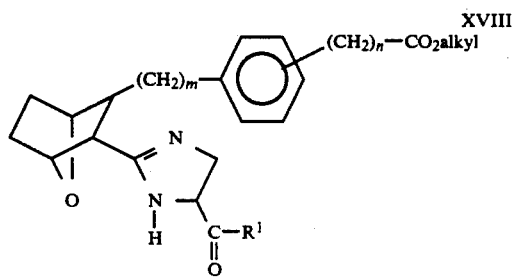

Compound XVIII is treated with an oxidizing agent such as manganese dioxide in the presence of an inert solvent such as chloroform to form compound I wherein X is NH, R² is CO₂R and R is alkyl.

Compounds of the invention wherein Y is —O— may be prepared as follows.

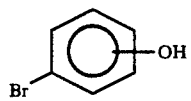

is treated with bromomethyl methyl ether to form the compound

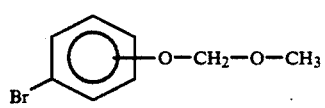

Compound B¹ is metallated (using a procedure similar to that set out above with respect to metal-halogen exchange of B using n-butyllithium in THF) and condensed with hemiacetal C to form the condensed 7-oxabicycloheptane compound

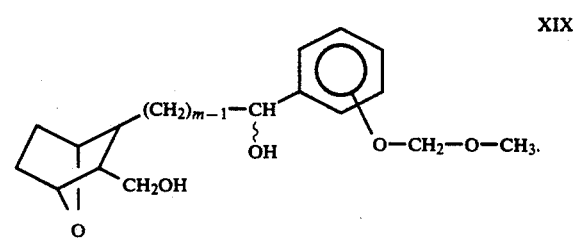

The condensed compound XIX is then subjected to hydrogenolysis by treatment with hydrogen in the presence of a catalyst such as palladium on charcoal in acetic acid, to form the alcohol

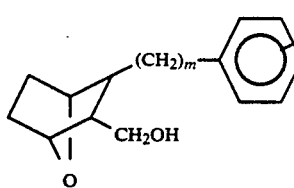

XX

Compound XX is deprotected by treatment with, for example, a solution of methanol and aqueous hydrochloric acid to form the deprotected alcohol

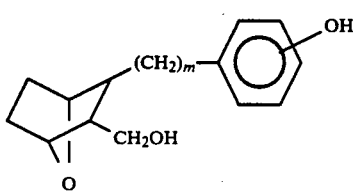

XXI

The alcohol XXI is then deprotonated by treating a solution of alcohol XXI in tetrahydrofuran with a molar equivalent of sodium hydride or one to four equivalents of a carbonate base such as potassium carbonate. The resulting phenoxide solution is alkylated by treating with a haloalkanoic acid ester G Halo—$(CH_2)_n$—$CO_2$alkyl employing a molar ratio of G:XXI of about 1:1 to 3:1 in the presence of an inert organic solvent (e.g., THF, dimethylformamide or dimethoxyethane) to form ester

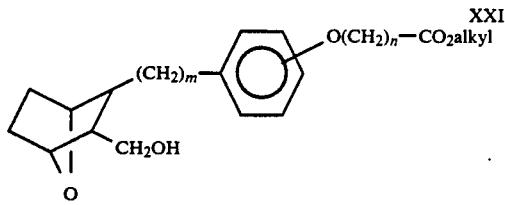

XXII

Alcohol ester XXII is treated as described above for compound VII to form compound I wherein Y is —O—.

Compounds of formula I wherein n is O and Y is —CH=CH— may be prepared starting with alcohol A wherein n is 2, which may be prepared by subjecting the aldehyde

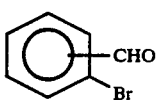

H to a Wittig reaction with $(C_6H_5)_3PCHCO_2CH_3$ to form the ester

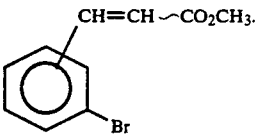

I

Ester I undergoes a double bond reduction by treatment with hydrogen in the presence of rhodium on alumina catalyst in the presence of methanol to form ester

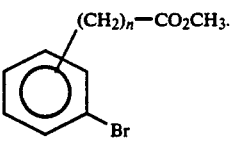

I[1]

Ester I[1] is then reduced by treatment with diisobutylaluminum hydride in the presence of toluene to form alcohol A wherein n is 2.

Alcohol A is used as described previously herein to form alcohol-ester VII wherein n is 2, which is treated with a silane protecting compound as described hereinbefore in the presence of an amine base (e.g., triethylamine) and an inert solvent (e.g., methylene chloride) and N,N-dimethylaminopyridine (DMAP) to form the protected alcohol

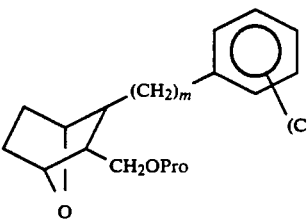

XXIII

The protected alcohol XXIII is then treated with lithium diisopropylamide in the form of a cooled (−78° to 0° C.) mixture of diisopropylamine and t-butyllithium or n-butyllithium under an inert atmosphere (e.g., argon). The resulting mixture is treated with diphenyl diselenide at about −78° to 25° C., to form the corresponding selenide

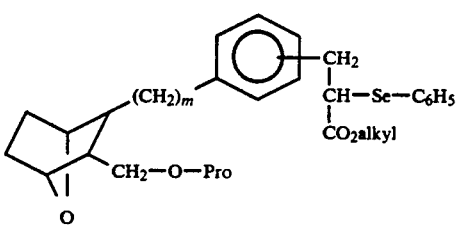

XXIV

Selenide XXIV in an inert organic solvent (e.g., ethyl acetate and/or methanol) is treated with an oxidizing agent (e.g., aqueous hydrogen peroxide) to form the cinnamate

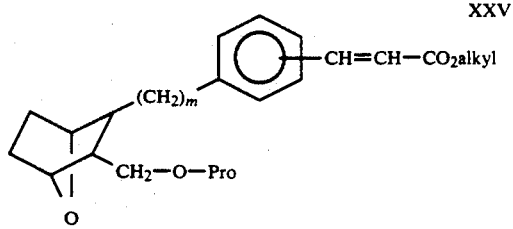

The protecting group is removed from cinnamate XXV with a fluoride (e.g., tetra-n-butylammonium fluoride) in an inert solvent such as THF to form the alcohol

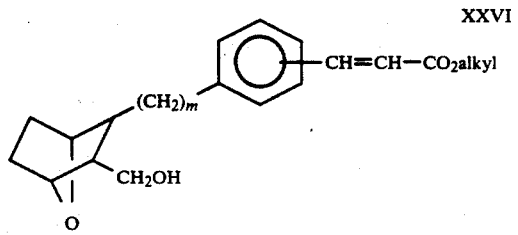

which may then be employed to form compounds of formula I wherein Y is —CH=CH—employing procedures described for treatment of alcohol-ester VII.

Compounds of the invention wherein n is 0 and Y is a single bond may be prepared starting with a bromobenzyl alcohol

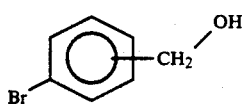

which is treated with a protecting compound (e.g., t-butylchlorodiphenylsilane) in the presence of 4-dimethylaminopyridine and an amine base (e.g., triethylamine) in an inert solvent (e.g., methylene chloride) to form the protected bromobenzyl compound

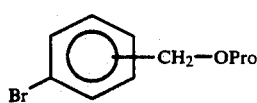

wherein Pro represents a protecting group.

Examples of protecting compounds suitable for use herein with the exclusion of benzyl bromide are as set out hereinbefore in reacting with bromophenalkyl alcohol A.

The protected compound $B^2$ is metallated by treatment with t-$C_4H_9$Li or n-$C_4H_9$Li in the presence of diethyl ether or THF at about $-100°$ to $0°$ C. or is subjected to a Grignard reaction by treatment with magnesium in the presence of an inert organic solvent such as THF or diethyl ether. The so-treated compound $B^2$ is then condensed with compound C in a C:$B^2$ molar ratio of about 1:2 to 1:4 in the presence of an inert organic solvent such as THF at about $-78°$ to $25°$ C. to form a condensed 7-oxabicycloheptane compound

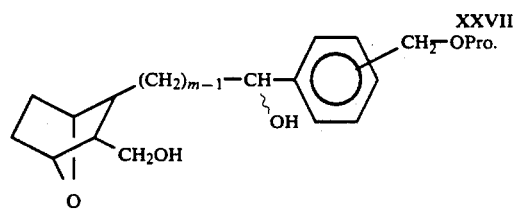

Compound XXVII is then protected by treatment with, for example, a solution of acetic anhydride and pyridine in the presence of 4-dimethylaminopyridine to form compound

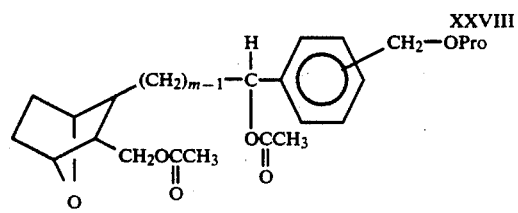

The protected alcohol XXVIII is then deprotected using conventional procedures, and the resulting alcohol is subjected to a Jones oxidation employing procedures described hereinbefore to form a crude acid. The crude acid is deacetylated by reaction with aqueous hydroxide in the presence of an inert organic solvent such as THF and then esterified, for example, by treatment with a diazoalkane (e.g., diazomethane) or acidic alcohol, to form the alcohol ester

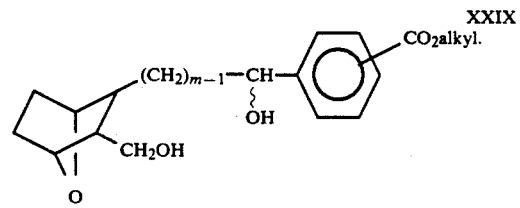

The alcohol ester XXIX is then subjected to hydrogenolysis as described above to provide the alcohol ester

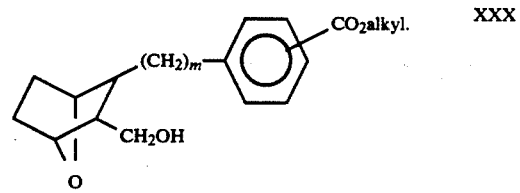

Next, the alcohol ester XXX is subjected to a Jones oxidation to form the acid ester

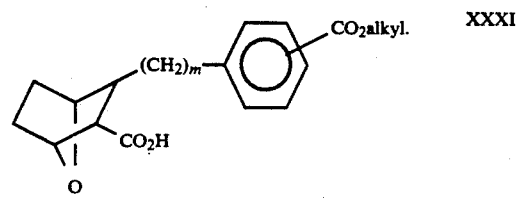

Acid ester XXXI is treated as described above for compound VIII to form compound I wherein Z is phenylene and n is O.

The compounds of formula I wherein Z is —CH=CH— or —(CH₂)₂— may be prepared as follows.

Compounds of the invention where Z is —CH=CH— and preferably in the cis form are prepared starting with the hydroxymethyl compound

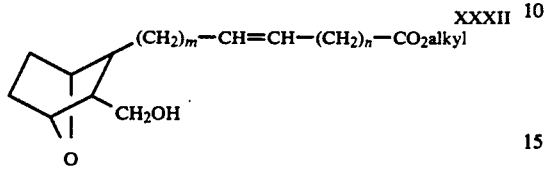

which is prepared as described in U.S. Pat. No. 4,143,054. Compound XXXII is subjected to a Jones oxidation with Jones' Reagent (CrO₃ dissolved or suspended in aqueous sulfuric acid, prepared as described in Fieser & Fieser, Reagents for Organic Synthesis, Vol I, p. 142 (1967)) in the presence of acetone under an inert atmosphere (e.g., argon) at about −10° to 20° C. to form the corresponding carboxylic acid-ester

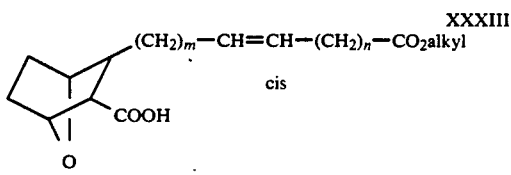

Acid-ester XXXIII is then reacted as described above for compound VIII to form compound I wherein Z is —CH=CH— in the cis double bond isomeric form.

The trans double bond isomer wherein Z is —CH=CH— in formula I may be prepared starting with hydroxymethyl compound XXXII, which includes a cis double bond. Compound XXXII is treated with a protecting compound such as t-butyldimethylsilyl chloride or other silyl protecting group as described hereinbefore in the presence of imidazole or triethylamine and an inert organic solvent such as methylene chloride or tetrahydrofuran, to form the protected compound

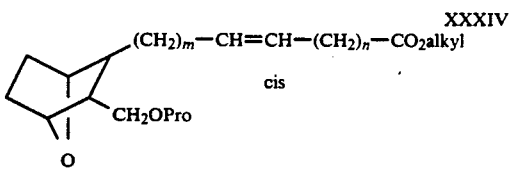

A solution of the protected alcohol in an inert organic solvent such as methylene chloride or acetone is treated with excess ozone at reduced temperature (about −78° to −60° C.) followed by treatment with dimethyl sulfide (molar ratio of XXXIV:(CH₃)₂S of about 0.01:1 to 0.2:1), to form the aldehyde

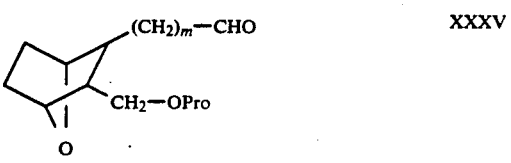

Aldehyde XXXV is then treated with a mixture of lithium bromide or lithium chloride and trimethylphosphonoacetate and triethylamine in an inert organic solvent such as methylene chloride or chloroform to form the ester

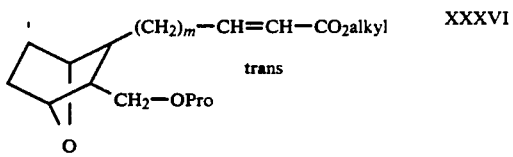

A solution of ester XXXVI in an inert organic solvent (e.g., tetrahydrofuran, diethyl ether or dimethyoxyethane) is cooled to about −78° to 0° C. and reacted with diisobutylaluminum hydride in an aromatic solvent such as toluene for about 0.5 to 4 hours to form alcohol

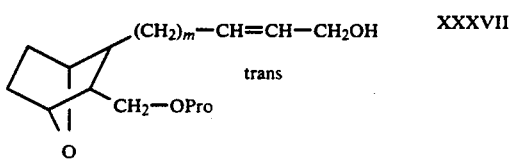

Alcohol XXXVII is treated with bromotriphenylphosphonium bromide (formed by adding bromine to triphenylphosphine in toluene or other aromatic solvent under argon at about −10° to 10° C.) in the presence of pyridine and toluene, at about −10° to 10° C. to form bromide

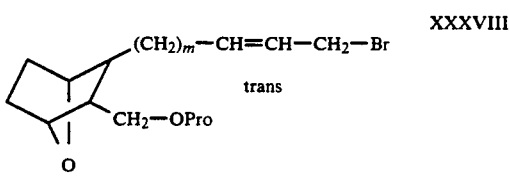

An acetic acid ester such as t-butyl acetate or ethyl acetate is treated with a solution of LDA (lithium diisopropylamide) in an inert organic solvent such as tetrahydrofuran and at about −78° to −60° C. for about 0.5 to 2 hours, followed by addition of a solution of bromide XXXVIII in an inert solvent such as tetrahydrofuran to form ester

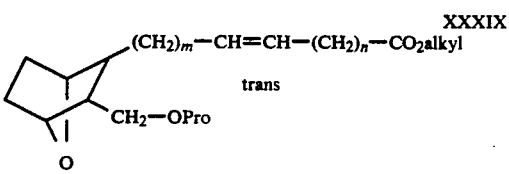

wherein n is 2.

For compounds of the invention wherein Z is —CH=CH— in the trans form and n is 1, 3, or 4, aldehyde XXXV is allowed to react with a phosphonium salt of formula

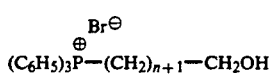

in the presence of a strong base such as potassium t-amylate in toluene or NaH/dimethylsulfoxide to give

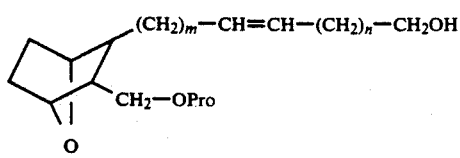

XL which is oxidized and esterified using procedures known in the art to form ester XXXIX wherein n is 1, 3 or 4.

Ester XXXIX is then deprotected by treatment in methanol under an inert atmosphere such as argon with hydrochloric acid in methanol (prepared by adding acetyl chloride to methanol) to form alcohol

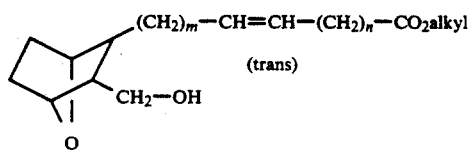

XLI

Alcohol XLI may then be used in place of compound XXXII as a starting material following the procedure hereinbefore described to form compound I wherein Z is —CH=CH— in the trans double bond isomeric form.

Compounds of formula I wherein Z is —(CH$_2$)$_2$— may be prepared from the corresponding acids wherein Z is —CH=CH— by hydrogenation using, for example, a hydrogenation catalyst (e.g., palladium on carbon) in an inert organic solvent (e.g., ethyl acetate or acetic acid).

Compounds of formula I wherein R$^2$ is CO$_2$R and R is alkali metal can be prepared from the corresponding esters by treating the ester with bases such as lithium hydroxide or potassium hydroxide. The corresponding acids (wherein R is hydrogen) are prepared by neutralizing the foregoing alkali metal salts with an acid (e.g., dilute hydrochloric acid or oxalic acid).

Compounds of the invention wherein R$^2$ is CONH-SO$_2$R$^3$ are prepared by treating the associated acids (wherein R$^2$ is CO$_2$H) with a sulfonamide

J in the presence of a coupling agent (e.g., carbonyldiimidazole or WSC) in the presence of an amine (e.g., DMAP) under an inert atmosphere (e.g., argon).

Compounds of formula I wherein R$^2$ is CONHR$^4$ wherein R$^4$ is other than hydrogen may be prepared from the corresponding acid by treatment with WSC in the presence of DMF, HOBT, an organic base (e.g., triethylamine) and an amine K

HNHR$^4$.

Where R$^4$ in compound I is hydrogen, ammonium chloride is used in place of amine K.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared with starting materials and procedures in U.S. Pat. No. 4,143,054.

The nucleus in each of the compounds of the invention is depicted as

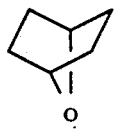

for convenience; the nucleus may also be depicted as

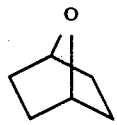

Use and Utility

The compounds of this invention are thromboxane receptor antagonists and as such are useful as inhibitors of thromboxane receptor mediated actions. The term "thromboxane receptor antagonist" includes compounds that are so-called thromboxane A$_2$ receptor antagonists, thromboxane A$_2$ antagonists, thromboxane A$_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstrition, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

PREFERRED EMBODIMENTS

The following Examples represent preferred embodiments of the present invention. Unless otherwise indicated, all temperatures are expressed in degrees Celsius.

EXAMPLE 1

[1S-(1α,2α, 3α, 4α)]-2-[[3-[4-(6-Cyclohexyl-1-oxohexyl)-2-oxazolyl]-7-oxabicyclo[2.2.1]hept-2-yl]methyl]benzenepropanoic acid, methyl ester A. 3-(2-Bromophenyl)-2-propenoic acid, methyl ester To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg), eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

B. 2-Bromobenzenepropanoic acid, methyl ester

A mixture of 201.5 g (836 mmol) of Part A acrylate and 8.4 g of 5% rhodium on alumina catalyst (MCB) in 1.0 L of methanol was stirred at room temperature under an atmosphere of hydrogen (balloon) for over 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight, the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water-soluble and gave a highly acid aqueous solution. Solid NaHCO$_3$ and Na$_2$SO$_4$ were carefully added (gas was evolved). The mixture was diluted with CH$_2$Cl$_2$, filtered, and evaporated (and re-evaporated with CH$_2$Cl$_2$ to drive off methanol) to obtain 196.9 g of clear oil. This oil was 95% pure title compound with 5% of the bromo title compound. The corrected yield of the title compound was 92% (187.1 g).

C. 2-Bromobenzenepropanol

To a stirred solution of 196.9 g (95% pure, 187.1 g, 770 mmol) of Part B compound in 770 mL of toluene under argon cooled to 0° (ice bath), was added over 45 minutes 830 mL of 1.0M diisobutylaluminum hydride (DIBAL-H) in toluene solution (830 mmol). The reaction was not very exothermic. After the mixture was stirred for 1 hour, TLC indicated approximately half of the starting material remained. Next, 580 mL of 1.5 M DIBAL-H in toluene solution (870 mmol) wa added slowly. The ice bath was removed and stirring was continued for 2 hours. The mixture was then poured slowly into 1.2 L of 6M aqueous HCl stirring in an ice bath. This quench was exothermic and gas was evolved. After the mixture was recooled to 0°, the layers were separated, and the organic layer was washed with 1M aqueous HCl and brine. It was then dried over $Na_2SO_4$ and $MgSO_4$ and evaporated (and re-evaporated with $CH_2Cl_2$ to drive off toluene) to obtain 173.0 g of a clear, colorless oil. This oil was 95% pure title compound with 5% of the part B title compound. The corrected yield of title compound was 99% (164.3 g).

D.
1-Bromo-2-[3-[[Dimethyl(1,1,2-trimethylpropyl)silyl]oxy]propyl]benzene

To a solution of 29.0 g (135 mmol) of the crude Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine and then 200 mg (1.64 mmol, Aldrich) of 4-dimethylaminopyridine. The reaction mixture was stirred at room temperature for 18 hours. The resulting slurry was diluted with 100 mL of hexane, cooled to 0° C. with stirring for 15 minutes, then filtered to remove solid triethylamine hydrochloride. The filtrate was concentrated in vacuo to give an oil. The crude oil was purified by flash chromatography (Merck silica, 15×10 cm, 1:9 ethyl acetate/petroleum ether) to afford 45.5 g (127 mmol, 94%) of the title compound as a colorless liquid.

E.
[1S-(1α,2α,3α,4α)]-[2-[3-[[Dimethyl(1,1,2-trimethylpropyl)silyl]oxy]propyl]phenyl]-7-oxabicyclo[2.2.1]heptane-2,3-dimethanol To a solution of 5.00 g (14.0 mmol) of compound D in 30 mL of dry diethyl ether (distilled mL (1.7M in pentane, 25 mmol, Aldrich) of t-butyllithium solution over 15 minutes. The reaction mixture was stirred at −100° C. for 15 minutes then at 0° C. for 15 minutes. The resulting pale yellow anion solution was recooled to −78° C., 30 mL of dry THF (distilled from ketyl) was introduced, and (3aα,4β,7β,7aα)]-octahydro-4,7-epoxyisobenzofuran-1-ol in 10 mL of THF was rapidly added. The reaction mixture was warmed to 0° C, stirred for 1 hour, quenched with 5 mL of water, then partitioned between 100 mL of water and 25 mL of ethyl acetate. The organic layer was separated and the aqueous layer was extracted with an additional 25 mL of ethyl acetate. The organic extracts were combined, dried (magnesium sulfate), and concentrated in vacuo to give an oil. The crude oil was purified by flash chromatography (Merck silica, 12×5.0 cm, 1:4 ethyl acetate/petroleum ether then 4:1 ethyl acetate/petroleum ether) to afford 2.35 g (5.41 mmol, 97%) of the title diastereomeric alcohols as a colorless oil.

F.
[1S-(1α,2α,3α,4α)]-2-[[2-[3-[[Dimethyl(1,1,2-trimethylpropyl)silyl]oxy]propyl]phenyl]methyl]-7-oxabicyclo[2.2.1]heptane-3-methanol A mixture of 1.90 g (4.38 mmol) of the Part E diastereomeric alcohols and 1.9 g of 20% palladium hydroxide on carbon catalyst (moist, less than 50% water, Aldrich) in 60 mL of glacial acetic acid was stirred rapidly under an atmosphere of hydrogen (balloon) for 5 hours. The reaction mixture was filtered through a 0.4 µM polycarbonate membrane and the filtrate was concentrated in vacuo (room temperature bath). The residue was partitioned between 50 mL of water and 50 mL of ethyl acetate. The organic layer was separated, washed with 50 mL of 1M aqueous sodium hydroxide solution, dried (magnesium sulfate), and concentrated in vacuo to give an oil. The crude material was purified by flash chromatography (Merck silica, 12×5.0 cm, 1:2 ethyl acetate/petroleum ether) to afford 1.03 g (2.39 mmol, 55%) of the title compound as a colorless oil. In addition, 573 mg (1.37 mmol, 30%) of the Part E starting material (as a single diastereomer) was recovered.

G.
[1S-(1α,2α,3α,4α)]-2-[[3-(Hydroxymethyl)-7-oxabicyclo[2.2.1]hept-2-yl]methyl]benzenepropanoic acid, methyl ester A solution of 1.00 g (2.39 mmol) of compound F and 50 mg (0.41 mmol, Aldrich) of 4-dimethylaminopyridine in 6 mL of 1:1 dry pyridine/acetic anhydride was stirred at room temperature for 2 hours. The reaction mixture was concentrated in vacuo and the residue partitioned between 25 mL of ethyl acetate and 20 mL of 1M aqueous HCl solution. The organic layer was separated, washed with 20 mL of 1M aqueous NaOH and 20 mL of brine, dried (magnesium sulfate), and concentrated in vacuo to afford the crude acetate as an oil.

To a solution of the crude acetate in 15 mL of reagent acetone cooled to 0° was added rapidly 3.3 mL of Jones reagent (2.6 M in $Cr^{+6}$, see Fieser & Fieser, *Reagents for Organic Synthesis*, Vol. 1, p. 142). The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 25 mL of diethyl ether and 25 mL of water. The organic layer was separated and concentrated in vacuo to give the crude acetate-acid as an oil.

A solution of the crude acetate-acid in 15 mL of 2:1 1M aqueous NaOH/THF was stirred at room temperature for 30 minutes. The reaction mixture was cooled in an ice-bath, quenched by 15 mL of 1M aqueous HCl solution, then extracted with two 25-mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0° C.) was stirred at 0° for 2 hours and then concentrated in vacuo. The resulting oil was purified by flash chromatography (Merck silica, 15×3.0 cm, ethyl acetate) to afford 526 mg (1.76 mmol, 74% from compound F) of the title compound as a colorless oil.

H.
[1S-(1α,2α,3α,4α)]-2-[[3-Carboxy-7-oxabicyclo[2.2.1]hept-2-yl]methyl]benzenepropanoic acid, methyl ester To a solution of 495 mg (1.63 mmol) of compound G in 5 mL of reagent acetone cooled to 0° C. was added rapidly 2.0 mL (2.6 M in $Cr^{+6}$) of Jones reagent. The reaction mixture was warmed to room temperature, stirred for 2 hours, then quenched by about 1 mL of isopropanol. After 15 minutes, the resulting green slurry was filtered through a pad of Celite. The filtrate was partitioned between 20 mL of diethyl ether and 20 mL of water. The organic layer was separated, and the aqueous layer was extracted with an additional 20 mL of diethyl ether. The ether extracts were combined, dried (magnesium sulfate), and concentrated in vacuo to give 560 mg (1.59 mmol, 98%) of crude title compound as a colorless oil.

I.
[1S-(1α,2α,3α,4α)]-2-[[3-[[1-(Hydroxymethyl)-2-oxo-2-(phenylmethoxy)ethyl]amino]carbonyl]-7-oxabicyclo[2.2.1]hept-2-yl]methyl]benzenepropanoic acid, methyl ester To a solution of 490 mg (1.54 mmol) of Part H acid in 10 mL of dry THF (distilled from ketyl) cooled to 0° was added 392 mg (1.69 mmol, Sigma) of L-serine benzyl ester hydrochloride, 228 mg (1.69 mmol, Aldrich) of 1-hydroxybenzotriazole hydrate and 530 μL (3.8 mmol, distilled from calcium hydride) of triethylamine. The mixture was stirred for 5 minutes, and then 348 mg (1.69 mmol, Aldrich) of dicyclohexylcarbodiimide was added in one portion. The reaction was stirred at 0° for 3 hours, then warmed to room temperature for 16 hours. The resulting slurry was diluted with 10 mL of ethyl acetate, cooled to 0° for 15 minutes then filtered. The filtrate was concentrated in vacuo to give an oil. The crude material was purified by flash chromatography (Merck silica, 15×3.0 cm, ethyl acetate) to afford 540 mg (1.09 mmol, 71%) of title compound as a white solid.

J.
[1S-(1α,2α,3α,4α)]-2-[[3-[4,5-Dihydro-4-[(phenylmethoxy)carbonyl]-2-oxazolyl]-7-oxabicyclo[2.2.1]hept-2-yl]methyl]benzenepropanoic acid, methyl ester To a solution of 525 mg (1.06 mmol) of Part I compound, 843 mg (3.10 mmol, Aldrich) of triphenylphosphine and 540 μL (3.1 mmol, Aldrich) of diisopropylethylamine in 6 mL of 5:1 dry acetonitrile/methylene chloride was added at room temperature 300 μL (3.1 mmol, Mallinckrodt) of reagent carbon tetrachloride. The reaction mixture was stirred for 2 hours then diluted with 15 mL of ethyl acetate followed by the slow addition of 15 mL of saturated aqueous sodium bicarbonate solution. The resulting mixture was stirred for 5 minutes then partitioned between 20 mL of ethyl acetate and 20 mL of water. The organic layer was separated, washed with 20 mL of brine, dried (sodium sulfate) and concentrated in vacuo to give a yellow oily solid. The crude material was purified by flash chromatography (Merck silica, 20×3.0 cm, 2:1 ethyl acetate/petroleum ether) to afford 380 mg (0.80 mmol, 75%) of title oxazoline as a pale yellow solid.

K.
[1S-(1α,2α,3α,4α)]-2-[[3-[4-[(Phenylmethoxy)carbonyl]-2-oxazolyl]-7-oxabicyclo[2.2.1]hept-2-yl]methyl]benzenepropanoic acid, methyl ester To a solution of 375 mg (0.79 mmol) of Part G oxazoline in 10 mL of dry methylene chloride (distilled from phosphorous pentoxide) was added 750 mg of nickel peroxide oxidant (K. Nakagawa et al, *J. Org. Chem.* 27 (1962), 1597) at room temperature. The reaction mixture was stirred for 1 hour, and then an additional 190 mg of oxidant was added. After 30 minutes, the reaction mixture was diluted with 20 mL of ethyl acetate, followed by 10 mL of 3M aqueous sodium bisulfite solution. The resulting mixture was stirred rapidly for 20 minutes, and then 10 mL of water was added. The organic layer was separated and the aqueous layer extracted with an additional 20 mL of ethyl acetate. The organic extracts were combined, washed with 25 mL of 1M aqueous sodium citrate solution, dried (magnesium sulfate) and concentrated in vacuo to give an oil. The crude material was purified by flash chromatography (Merck silica, 15×5.0 cm, 2:3 ethyl acetate/petroleum ether) to afford 180 mg (0.38 mmol, 48%) of title oxazole as an oil.

L.
[1S-(1α,2α,3α,4α)]-2-[[3-[4-Carboxyl]2-oxazolyl]-7-oxabicyclo[2.2.1]hept-2-yl]methyl]benzenepropanoic acid, methyl ester To a solution of 7.68 g (16.2 mmol) of benzyl ester K in 100 mL reagent ethyl acetate (Mallinckrodt), stirred at room temperature under argon, was added 770 mg (0.1 equivalent by weight) of 20% palladium hydroxide on carbon catalyst. The reaction vessel was evacuated and filled with hydrogen three times, then stirred under a hydrogen atmosphere (balloon) for 3.5 hours. The resulting slurry was purged with argon, then diluted with 250 mL ethyl acetate and warmed to dissolve the white precipitate (product). The warm mixture was filtered through a Buchner funnel, then through a 0.4 μM polycarbonate filter. The filtrate was concentrated in vacuo to give a white solid. The crude solid was slurried in 125 mL ethyl acetate and filtered. The white solid was collected; the filtrate was concentrated, slurried with 50 mL ethyl acetate and filtered to recover more product. This procedure was repeated once more. The combined white solid was dried under vacuum to give 5.39 g (13.9 mmol, 87%) of acid L as a white solid, melting point 170°–171° C.

[1S-(1α,2α,3α,4α)]-2-[[3-[4-Chlorocarbonyl]-2-oxazolyl]-7-oxabicyclo[2.2.1]hept-2-yl]methyl]benzenepropanoic acid, methyl ester To a solution of 500 mg (1.29 mmol) of acid L in 20 mL dry methylene chloride (distilled from $P_2O_5$) was added 1 small drop of dimethylformamide, followed by 780 μL (1.56 mmol, 2M/methylene chloride, Aldrich) of oxalyl chloride solution. The reaction was stirred at room temperature until gas evolution ceased (about 30 minutes), then the mixture was concentrated in vacuo to give the crude acid chloride title compound as a pale yellow solid.

N. 5-Cyclohexyl-1-pentanol

To a portion of 100 mL glacial acetic acid, purged with argon, was added 5.62 g of $PtO_2$ (Aldrich) followed by a solution of 25.00 g (152.2 mmol, Aldrich) of 5-phenyl-1-pentanol in 100 mL glacial acetic acid. The reaction vessel was evacuated and purged with $H_2$ three times, the the reaction mixture was stirred under $H_2$ (1 atm) of 22 hours. The reaction was not complete by thin layer chromatography. A second portion of 3.25 (Aldrich) of $PtO_2$ was added and the reaction was stirred under $H_2$ (1 atm) for an additional 32 hours. The mixture was filtered through a 0.4 μM polycarbonate filter, the filtrate was concentrated in vacuo and then azeotroped four times with toluene to give 28.08 g (164.9 mmol, 100%) of a cloudy liquid. $^1H$ NMR indicated the crude material was about a 2:1 mixture of the alcohol title compound and the corresponding acetate.

To a solution of this alcohol/acetate mixture in 160 mL distilled tetrahydrofuran/40 mL water was added 4.93 g (117.5 mmol, Aldrich) of lithium hydroxide monohydrate. The reaction was stirred vigorously for 24 hours at room temperature. TLC showed the reaction was not complete. A second portion of 2.46 g (58.7 mmol, Aldrich) of lithium hydroxide monohydrate was added to the reaction. The reaction was stirred for another 12 hours, then quenched by the addition of 325 mL (325 mmol) 1M hydrochloric acid. The mixture was partitioned between 300 mL ethyl acetate/300 mL water; the water layer was separated and washed with two 150-mL portions of ethyl acetate. The combined ethyl acetate layers were dried (magnesium sulfate) and concentrated in vacuo to give 25.32 g (148.7 mmol, 98%) of the alcohol title compound as a clear liquid.

O. 5-Cyclohexyl-1-bromopentane

A mixture of 25.32 g (149.7 mmol) of alcohol N, 10.1 mL of concentrated sulfuric acid and 32.3 mL of 48% hydrobromic acid was refluxed for 23 hours. The reaction mixture was partitioned between 300 mL water/300 mL hexane; the water layer was separated and washed with two 150-mL portions of hexane. The combined hexane layers were washed with 400 mL 1M sodium hydroxide, dried (magnesium sulfate) and concentrated in vacuo to give a clear brown liquid. The crude liquid was flash-chromatographed (Merck silica, hexane) to give a cloudy liquid, which was distilled (Kugelrohr, 132°, 3.5 mmHg) to give 22.07 g (94.60 mmol, 64%) of the bromide title compound as a clear liquid.

P. [1S-(1α,2α,3α,4α)]-2-[[3-[4-(6-Cyclohexyl-1-oxohexyl)-2-oxazolyl]-7-oxabicyclo[2.2.1]hept-2-yl]methyl]benzenepropanoic acid, methyl ester In an oven-dried, three-necked round bottom flask was placed 2.08 g (85.8 mmol, Mallinckrodt) of magnesium turnings, followed by 20 mL dry ether (distilled from Na, Ph₂CO). The reaction was initiated by the addition of three drops of dibromoethane (Aldrich), one iodine crystal (Aldrich) and slight agitation, followed by the slow, dropwise addition of 10.00 g (42.88 mmol) of bromide O. The reaction was slightly exothermic. After addition of bromide, the reaction mixture was refluxed for 3 hours, cooled to room temperature and transferred to an airtight bottle. Addition of a portion of the Grignard solution to water followed by acid titration (phenolphthalein) gave a concentration of 1.65M.

In an oven-dried, three-necked round bottom flask was placed 1.81 mL (1.81 mmol, 1M/ether, Aldrich) of zinc chloride solution and 5 mL dry ether (distilled from Na, Ph₂CO). To this solution was added dropwise 1.09 mL (1.81 mmol, 1.65M/ether) of the Grignard reagent over 10 minutes. The reaction mixture was refluxed for 1.5 hours, then a solution of crude acid chloride M (about 1.29 mmol) in 25 mL sieve-dried benzene was added dropwise over 15 minutes. The mixture was stirred for 12 hours at room temperature, then refluxed for 8 hours. The reaction mixture was cooled and partitioned between 150 mL methylene chloride/150 mL 1M hydrochloric acid. The organic layer was separated, washed with 100 mL saturated sodium hydrogen carbonate solution, dried (magnesium sulfate) and concentrated in vacuo to give a crude yellow oil. The crude oil was flash-chromatographed (Merck silica, 1:4 ethyl acetate/hexane) to give 130 mg of an impure white solid (TLC showed a small amount of a higher Rf impurity). The impure solid was recrystallized (hot hexane/ethyl acetate) to give 69 mg (0.13 mmol, 10% of ketone P as a white solid, melting point 105 to 107°.

EXAMPLE 2

[1S-(1α,2α,3α,4α)]-2-[3-[4-(6-Cyclohexyl-1-oxohexyl)-2-oxazolyl]-7-oxabicyclo[2.2.1]hept-2-yl]methyl]benzenepropanoic acid To a solution of 66 mg (0.13 mmol) of ester Example 1 in 4 mL distilled tetrahydrofuran/1 mL water was added 11 mg (0.25 mmol, Aldrich) of lithium hydroxide monohydrate. The reaction was stirred vigorously for 2.5 hours at room temperature, then quenched by the addition of 0.51 mL (0.51 mmol) 1M hydrochloric acid. The mixture was partitioned between 15 mL ethyl acetate/15 mL water. The water layer was separated and extracted with an additional 15 mL portion of ethyl acetate. The combined ethyl acetate layers were separated, dried (magnesium sulfate) and concentrated in vacuo to give 52 mg (0.10 mmol, 81%) of acid Example 2, as a white solid, melting point 155°–158°.

IR (KBr): 3433, 3076, 2922, 2B50, 1710, 1689, 1579 cm⁻¹.

OR: [α]$_D$ = +31° (c = 0.5 in methylene chloride).

TLC: R$_f$ (silica gel, 1:9 methanol/methylene chloride) = 0.61, ammonium molybdate/ceric sulfate and UV, homogeneous.

Analysis for $C_{31}H_{41}NO_5$: Calc'd: C,73.34; H,8.14; N,2.76. Found: C,73.25; H,8.25; N,2.68.

What is claimed is:

1. A compound having the formula

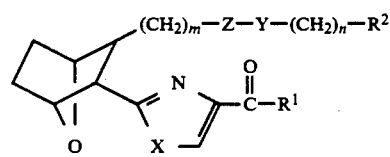

and all steroisomers and pharmaceutically acceptable salts thereof, wherein:
m is 1, 2, or 3;
n is 0, 1, 2 or 3;
X is O or NH;
Y is —O—, a single bond or vinylene, except that Y cannot be —O— when n is 0;
Z is —CH=CH—, —(CH₂)₂—, or

R¹ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, each of R¹ being unsubstituted or optionally substituted with alkyl, aryl, cycloalkyl, or cycloalkylalkyl;
R² is CO₂R, CONHSO₂R³, or CONHR⁴;
R is hydrogen, alkyl, or alkali metal;
R³ is alkyl, aryl or aralkyl; and
R⁴ is hydrogen, alkyl, aryl or aralkyl;
and wherein:

"cycloheteroalkyl" refers to 5-, 6- or 7-membered saturated rings having 1 or 2 heteroatoms selected from nitrogen, oxygen and sulfur, and which are linked through a carbon atom either beta or gamma to a heteroatom;

"heteroaryl" refers to 5- or 6-membered aromatic rings having 1 or 2 heteroatoms selected from nitrogen, oxygen and sulfur, which are not directly linked through a heteroatom;

"cycloheteroalkylalkyl" refers to 5-, 6- or 7-membered saturated rings having 1 or 2 heteroatoms selected from nitrogen, oxygen and sulfur, and are linked through a $(CH_2)_x$ chain wherein x is 1 to 12; and "heteroarylalkyl" refers to 5-, 6- or 7-membered aromatic rings having 1 to 4 heteroatoms selected from 1 to 4 nitrogen and 1 or 2 oxygen or sulfur atoms, and which are linked through a —$(CH_2)_x$— chain where x is 1 to 12.

2. The compound of claim 1 having the formula

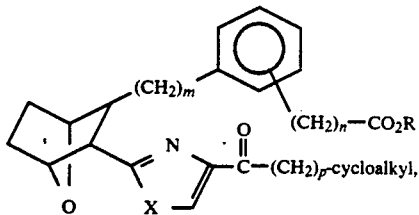

wherein p is an integer from 1 to 7.

3. The compound of claim 1, wherein m is 1.
4. The compound of claim 2, wherein m is 1.
5. The compound of claim 2, wherein p is 5.
6. The compound of claim 1, wherein n is 2.
7. The compound of claim 2, wherein n is 2.
8. The compound of claim 1, wherein $R^2$ is $CO_2R$.
9. The compound of claim 2, wherein R is hydrogen.
10. The compound of claim 8, wherein R is hydrogen.
11. The compound of claim 2, wherein the cycloalkyl group is cyclohexane.
12. The compound of claim 1, having the names:
[1S-(1α,2α, 3α, 4α)]-2-[[3-[4-(6-Cyclohexyl-1-oxohexyl)-2-oxazolyl]-7-oxabicyclo[2.2.1]hept-2-yl]methyl]benzenepropanoic acid, methyl ester, and
[1S-(1α,2α, 3α, 4α)]-2-[[3-[4-(6-Cyclohexyl-1-oxohexyl)-2-oxazolyl]-7-oxabicyclo[2.2.1]hept-2-yl]methyl]benzenepropanoic acid.

* * * * *